(12) United States Patent
Yasovsky et al.

(10) Patent No.: US 9,528,906 B1
(45) Date of Patent: Dec. 27, 2016

(54) MONITORING DOE PERFORMANCE USING TOTAL INTERNAL REFLECTION

(71) Applicant: Apple Inc., Cupertino, CA (US)

(72) Inventors: Alon Yasovsky, Rehovot (IL); Benny Pesach, Rosh Haayin (IL)

(73) Assignee: APPLE INC., Cupertino, CA (US)

( * ) Notice: Subject to any disclaimer, the term of this patent is extended or adjusted under 35 U.S.C. 154(b) by 224 days.

(21) Appl. No.: 14/548,476

(22) Filed: Nov. 20, 2014

Related U.S. Application Data

(60) Provisional application No. 61/917,953, filed on Dec. 19, 2013.

(51) Int. Cl.
G02B 27/44 (2006.01)
G01M 11/02 (2006.01)
G01J 1/04 (2006.01)
G02B 27/42 (2006.01)

(52) U.S. Cl.
CPC ......... *G01M 11/0207* (2013.01); *G01J 1/0407* (2013.01); *G02B 27/4205* (2013.01)

(58) Field of Classification Search
CPC  G01M 11/0207; G01J 1/0407; G02B 27/4205
USPC .......................................... 250/206; 359/565
See application file for complete search history.

(56) References Cited

U.S. PATENT DOCUMENTS

| 3,796,498 A | 3/1974 | Post |
| 4,850,673 A | 7/1989 | Velzel et al. |
| 5,406,543 A | 4/1995 | Kobayashi et al. |
| 5,477,383 A | 12/1995 | Jain |
| 5,606,181 A | 2/1997 | Sakuma et al. |
| 5,648,951 A | 7/1997 | Kato et al. |
| 5,691,989 A | 11/1997 | Rakuljic et al. |
| 5,742,262 A | 4/1998 | Tabata et al. |
| 5,781,332 A | 7/1998 | Ogata |
| 6,002,520 A | 12/1999 | Hoch et al. |
| 6,031,611 A | 2/2000 | Rosakis |

(Continued)

FOREIGN PATENT DOCUMENTS

| CN | 1725042 A | 1/2006 |
| JP | 2008300106 A | 12/2008 |

(Continued)

OTHER PUBLICATIONS

Fienup, J.R., "Phase Retrieval Algorithms: A Comparison", Applied Optics, vol. 21, No. 15, Aug. 1, 1982.

(Continued)

*Primary Examiner* — Seung C Sohn
(74) *Attorney, Agent, or Firm* — D. Kligler IP Services Ltd.

(57) ABSTRACT

Optical apparatus includes a diffractive optical element (DOE), which includes multiple optical surfaces, including at least an entrance surface and an exit surface, and a side surface, which is not parallel to the optical surfaces of the DOE. A grating is formed on at least one of the optical surfaces so as to receive radiation entering the DOE via the entrance surface and to diffract the radiation into a predefined pattern comprising multiple diffraction orders that exit the DOE via the exit surface. An optical detector is positioned in proximity to the side surface so as to receive and sense an intensity of a high order of the radiation diffracted from the grating that passes through the side surface of the DOE.

17 Claims, 2 Drawing Sheets

(56) References Cited

U.S. PATENT DOCUMENTS

| | | | |
|---|---|---|---|
| 6,462,874 B1 * | 10/2002 | Soskind | G02B 5/1814 359/565 |
| 6,560,019 B2 | 5/2003 | Nakai | |
| 6,583,873 B1 | 6/2003 | Goncharov et al. | |
| 6,611,000 B2 | 8/2003 | Tamura et al. | |
| 6,664,998 B1 | 12/2003 | Kyoya et al. | |
| 6,707,027 B2 | 3/2004 | Liess et al. | |
| 6,927,852 B2 | 8/2005 | Reel | |
| 6,940,583 B2 | 9/2005 | Butt et al. | |
| 7,112,774 B2 | 9/2006 | Baer | |
| 7,149,030 B2 * | 12/2006 | Kleemann | G02B 5/1828 359/566 |
| 7,227,618 B1 | 6/2007 | Bi | |
| 7,304,735 B2 | 12/2007 | Wang et al. | |
| 7,335,898 B2 | 2/2008 | Donders et al. | |
| 7,700,904 B2 | 4/2010 | Toyoda et al. | |
| 7,952,781 B2 | 5/2011 | Weiss et al. | |
| 8,106,993 B2 * | 1/2012 | Korenaga | G02B 3/0068 348/335 |
| 8,492,696 B2 | 7/2013 | Akerman et al. | |
| 8,630,039 B2 | 1/2014 | Shpunt | |
| 8,749,796 B2 | 6/2014 | Pesach et al. | |
| 8,829,406 B2 | 9/2014 | Akerman et al. | |
| 8,908,277 B2 | 12/2014 | Pesach et al. | |
| 2004/0012958 A1 | 1/2004 | Hashimoto et al. | |
| 2004/0082112 A1 | 4/2004 | Stephens | |
| 2005/0178950 A1 | 8/2005 | Yoshida | |
| 2006/0001055 A1 | 1/2006 | Ueno et al. | |
| 2006/0252167 A1 | 11/2006 | Wang | |
| 2006/0252169 A1 | 11/2006 | Ashida | |
| 2006/0269896 A1 | 11/2006 | Liu et al. | |
| 2007/0019909 A1 | 1/2007 | Yamauchi et al. | |
| 2008/0198355 A1 | 8/2008 | Domenicali et al. | |
| 2008/0212835 A1 | 9/2008 | Tavor | |
| 2008/0240502 A1 | 10/2008 | Freedman et al. | |
| 2008/0278572 A1 | 11/2008 | Gharib et al. | |
| 2009/0090937 A1 | 4/2009 | Park | |
| 2009/0096783 A1 | 4/2009 | Shpunt et al. | |
| 2009/0183125 A1 | 7/2009 | Magal et al. | |
| 2009/0185274 A1 | 7/2009 | Shpunt | |
| 2010/0007717 A1 | 1/2010 | Spektor et al. | |
| 2010/0013860 A1 | 1/2010 | Mandella et al. | |
| 2010/0142014 A1 | 6/2010 | Rosen et al. | |
| 2010/0284082 A1 | 11/2010 | Shpunt et al. | |
| 2011/0019258 A1 | 1/2011 | Levola | |
| 2011/0069389 A1 | 3/2011 | Shpunt | |
| 2011/0187878 A1 | 8/2011 | Mor et al. | |
| 2011/0188054 A1 | 8/2011 | Petronius et al. | |
| 2011/0295331 A1 | 12/2011 | Wells et al. | |
| 2012/0038986 A1 | 2/2012 | Pesach | |
| 2012/0140109 A1 | 6/2012 | Shpunt et al. | |
| 2013/0127854 A1 | 5/2013 | Shpunt et al. | |
| 2013/0250387 A1 | 9/2013 | Chayat et al. | |
| 2014/0022348 A1 | 1/2014 | Shpunt | |

FOREIGN PATENT DOCUMENTS

| | | |
|---|---|---|
| JP | 2011118178 A | 6/2011 |
| WO | 2007/043036 A1 | 4/2007 |
| WO | 2007/105205 A2 | 9/2007 |
| WO | 2008/120217 A2 | 10/2008 |
| WO | 2010/004542 A1 | 1/2010 |
| WO | 2012020380 A1 | 2/2012 |

OTHER PUBLICATIONS

Btendo, "Two Uni-axial Scanning Mirrors Vs One Bi-axial Scanning Mirror", Kfar Saba, Israel, Aug. 13, 2008.

Ezconn Czech A.S. "Site Presentation", Oct. 2009.

Gerchberg et al., "A Practical Algorithm for the Determination of the Phase from Image and Diffraction Plane Pictures," Optik 35 (1972), pp. 237-246.

Sazbon et al., "Qualitative Real-Time Range Extraction for Preplanned Scene Partitioning Using Laser Beam Coding," Pattern Recognition Letters 26 (2005), pp. 1772-1781.

Moharam et al. "Rigorous coupled-wave analysis of planar-grating diffraction", Journal of the Optical Society of America, vol. 71, No. 6, pp. 818-818, Jul. 1981.

Luxtera Inc., "Luxtera Announces World's First 10GBit CMOS Photonics Platform", Carlsbad, USA, Mar. 28, 2005 (press release).

Eisen et al., "Total internal reflection diffraction grating in conical mounting", Optical Communications 261, pp. 13-18, year 2006.

O'Shea et al., "Diffractive Optics: Design, Fabrication and Test", SPIE Tutorial Texts in Optical Engineering, vol. TT62, pp. 66-72, SPIE Press, USA 2004.

Microvision Inc., "Micro-Electro-Mechanical System (MEMS) Scanning Mirror", 1996-2009.

Japanese Patent Application # 2010-251347 Office Action dated Feb. 5, 2014.

U.S. Appl. No. 13/936,234 Office Action dated May 13, 2014.

Bradley et al., "Synchronization and Rolling Shutter Compensation for Consumer Video Camera Arrays", IEEE International Workshop on Projector-Camera Systems—PROCAMS 2009, Miami Beach, Florida, 2009.

Marcia et al., "Fast Disambiguation of Superimposed Images for Increased Field of View", IEEE International Conference on Image Processing, San Diego, USA, Oct. 12-15, 2008.

U.S. Appl. No. 12/945,908 Official Action dated Dec. 5, 2012.

Garcia et al.., "Projection of Speckle Patterns for 3D Sensing", Journal of Physics, Conference series 139, 2008.

Garcia et al., "Three-dimensional mapping and range measurement by means of projected speckle patterns", Applied Optics, vol. 47, No. 16, pp. 3032-3040, Jun. 1, 2008.

\* cited by examiner

MONITORING DOE PERFORMANCE USING TOTAL INTERNAL REFLECTION

CROSS-REFERENCE TO RELATED APPLICATION

This application claims the benefit of U.S. Provisional Patent Application 61/917,953, filed Dec. 19, 2013, which is incorporated herein by reference.

FIELD OF THE INVENTION

The present invention relates generally to diffractive optics, and specifically to monitoring the performance of a diffractive optical element (DOE).

BACKGROUND

Diffractive optics are used in a wide variety of applications. In some applications, diffractive optical elements (DOEs) are used in creating a desired projection pattern, for purposes such as optical three-dimensional (3D) mapping, area illumination, and LCD backlighting. DOE-based projector designs are described, for example, in U.S. Patent Application Publication 2009/0185274, whose disclosure is incorporated herein by reference.

The "efficiency" of a DOE is a measure of the amount of input energy that the DOE diffracts, in relation to the energy of the incoming beam. This efficiency can vary in production due to manufacturing tolerances. It can also change during the lifetime and operation of the DOE for various reasons. For example, humidity and other vapors can condense on the DOE surface and lower its efficiency, or excess heat, due to a malfunction or misuse, can deform the DOE and change its efficiency. Such changes in efficiency can result in undesirable increases in the intensity of the zero diffraction order, which is not diffracted by the projection optics and may thus continue straight through the DOE to the projection volume.

U.S. Pat. No. 8,492,696, whose disclosure is incorporated herein by reference, describes a DOE-based projector with a built-in beam monitor, in the form of an integral optical detector. The detector signal can be continuously or intermittently monitored by a controller in order to evaluate the DOE efficiency and inhibit operation of the projector if the signal is outside a certain safe range. Such embodiments are said to prevent eye safety hazards that could otherwise arise due to DOE efficiency degradation over the lifetime of the projector.

SUMMARY

Embodiments of the present invention provide improved methods and devices for monitoring the performance of a DOE.

There is therefore provided, in accordance with an embodiment of the invention, optical apparatus, which includes a diffractive optical element (DOE), including multiple optical surfaces, which include at least an entrance surface and an exit surface, and a side surface, which is not parallel to the optical surfaces of the DOE. A grating is formed on at least one of the optical surfaces so as to receive radiation entering the DOE via the entrance surface and to diffract the radiation into a predefined pattern including multiple diffraction orders that exit the DOE via the exit surface. An optical detector is positioned in proximity to the side surface so as to receive and sense an intensity of a high order of the radiation diffracted from the grating that passes through the side surface of the DOE.

Typically, the side surface is perpendicular to the optical surfaces of the DOE.

In some embodiments, the optical detector includes a front surface that is in contact with the side surface of the DOE.

In the disclosed embodiments, the optical surfaces of the DOE are configured so that the high order of the diffracted radiation reaches the side surface after reflecting internally within the DOE.

In some embodiments, the apparatus includes a controller, which is coupled to receive a signal from the optical detector that is indicative of the intensity of the high order of the diffracted radiation and to monitor a performance of the DOE responsively to the signal. The apparatus may also include a radiation source, which is configured to direct the radiation toward the entrance surface of the DOE, wherein the controller is coupled to control an operation of the radiation source responsively to the monitored performance.

Typically, the controller is configured to inhibit the operation of the radiation source when the signal is outside a predefined range. In a disclosed embodiment, the diffraction orders that exit the DOE via the exit surface include a zero order, and a change of the signal is indicative of an increase of an intensity of the zero order, and the controller is configured to inhibit the operation of the radiation source when the change exceeds a predefined threshold.

There is also provided, in accordance with an embodiment of the invention, an optical method, which includes transmitting radiation through a diffractive optical element (DOE), which includes multiple optical surfaces, including at least an entrance surface and an exit surface, and which includes a grating, which is formed on at least one of the optical surfaces so as to receive the radiation entering the DOE via the entrance surface and to diffract the radiation into a predefined pattern including multiple diffraction orders that exit the DOE via the exit surface. An intensity is received and sensed of a high order of the radiation diffracted from the grating that passes through a side surface of the DOE, which is not parallel to the optical surfaces of the DOE.

The present invention will be more fully understood from the following detailed description of the embodiments thereof, taken together with the drawings in which:

DETAILED DESCRIPTION OF EMBODIMENTS

Figure 1:
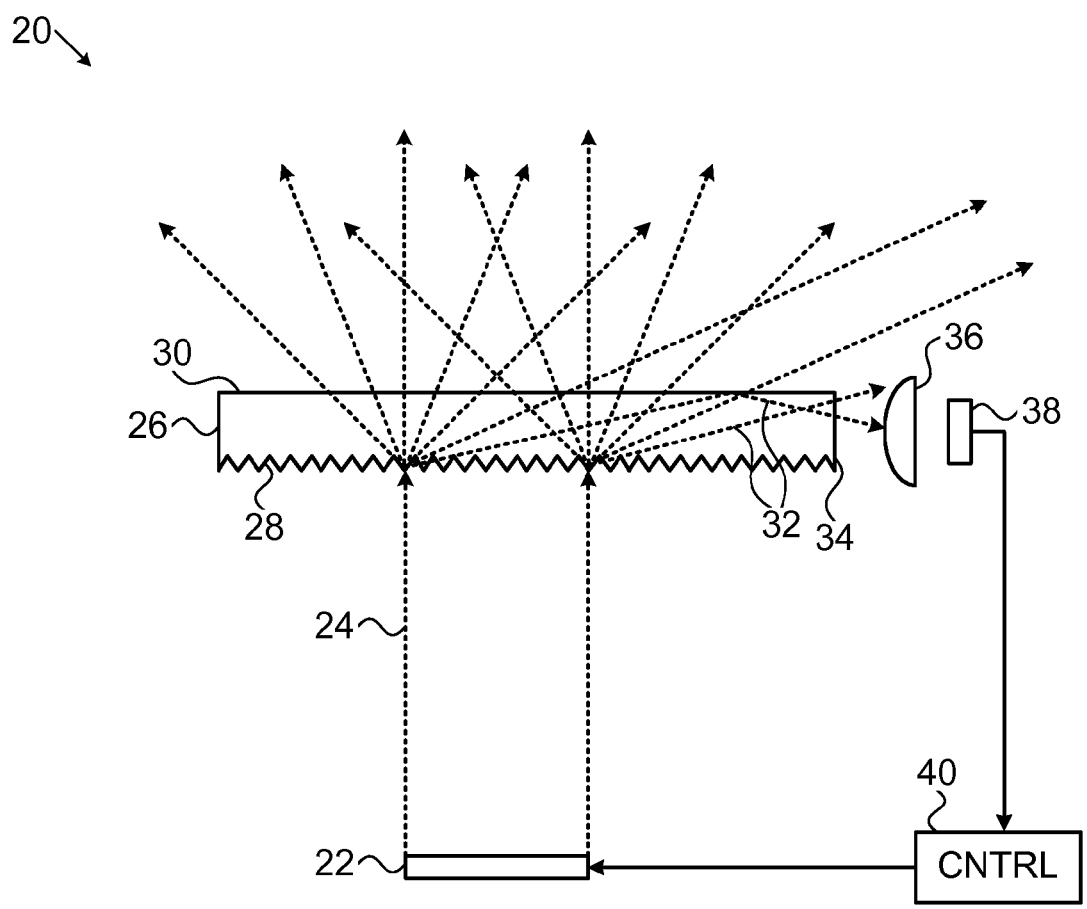
FIG. 1 is a schematic side view of an optical projector with a beam monitor, in accordance with an embodiment of the present invention.

Optical projectors based on diffractive optical elements (DOEs) sometimes suffer from the "zero-order problem," which is described in the above-mentioned US 2009/0185274: A portion of the input beam of the projector (the zero diffraction order) may not be diffracted by the projection optics and may thus continue through to the projection volume. Changes in efficiency of a DOE, with concomitant increases in the zero-order intensity, can compromise system performance and may have various other undesirable consequences.

Any DOE comprises multiple optical surfaces, including at least an entrance surface and an exit surface. The diffractive effect of the DOE is provided by a grating formed on one of these optical surfaces (which may be the entrance surface, the exit surface, or an internal surface within the DOE), or by multiple gratings on multiple optical surfaces. Such gratings may have any suitable shape and form, depending on the diffraction pattern that the DOE is to create. The gratings receive radiation entering the DOE via the entrance surface and diffract the radiation into a predefined pattern comprising multiple diffraction orders that exit the DOE via the exit surface.

In a typical configuration, the grating and the optical surfaces of a DOE are arranged so that the diffraction orders that exit the DOE via the exit surface are the lower orders (including at least the zero order and first orders of diffraction). These orders define the diffraction pattern that is projected through the exit surface by the DOE. The grating may be designed to suppress the higher orders, but typically at least some high-order radiation is diffracted from the grating at a high angle, within the DOE. (A "high order" in this context means at least the second diffraction order, or possibly the third, fourth, or still higher order.) Some of this high-order radiation may reach the side surfaces of the DOE, i.e., surfaces that are not parallel to the optical surfaces and are outside the path of the intended diffraction pattern. In many cases, these high orders reach the side surface by total internal reflection within the DOE.

Embodiments of the present invention that are described hereinbelow take advantage of this "leakage" of high diffraction orders to the side surfaces, typically in order to monitor the performance of the DOE. In the disclosed embodiments, an optical detector is positioned in proximity to a side surface of the DOE so as to receive and sense the intensity of the high-order diffracted radiation passing through the side surface. This approach is advantageous in that it enables the performance of the DOE to be monitored using only minimal additional hardware, and possibly with only minimal impact on the size and cost of the overall DOE assembly.

In some embodiments, a controller receives from the optical detector a signal that is indicative of the intensity of the high orders of the diffracted radiation, and thus monitors the performance of the DOE. Based on this signal, the controller may control the operation of the radiation source that provides the input radiation to the DOE and may inhibit the operation of the radiation source when the signal is outside a predefined range. For example, a decrease in the signal from the detector may be indicative of a loss of efficiency of the DOE, which may lead to an increase in the intensity of the zero order, as explained above. (On the other hand, in other cases, severe failure of the DOE may lead to increased scatter, giving an increased detector signal.) In such cases, the controller will typically inhibit the operation of the radiation source when the signal changes by more than a certain threshold, possibly by simply turning the radiation source off.

FIG. 1 is a schematic side view of an optical projector 20 with a beam monitor, in accordance with an embodiment of the present invention. A radiation source emits a beam 24 of radiation toward a DOE 26. Typically, the radiation is coherent optical radiation in the visible, infrared or ultraviolet range (the spectral regions that are generally referred to as "light"). Radiation source 22 may comprise a laser diode, for example, or an array of laser diodes, such as a vertical-cavity surface-emitting laser (VCSEL) array.

DOE 26 comprises a transparent substrate, such as glass or a suitable plastic, for example polycarbonate, with a grating 28 formed on one of its optical surfaces. In the pictured example, grating 28 is formed on the entrance surface of DOE 26, facing radiation source 22, and generates a pattern comprising multiple diffraction orders, which exit DOE 26 through an exit surface 30. Alternatively or additionally, as noted earlier, DOE 26 may comprise one or more gratings formed on exit surface or on one or more internal optical surfaces (not shown). The gratings may be configured, for example, to generate multiple, adjacent instances of a pattern of spots, as described in U.S. Pat. No. 8,384,997, whose disclosure is incorporated herein by reference. Such patterns are useful particularly in 3D mapping (in association with an imaging assembly), as described in U.S. Pat. No. 8,384,997 and in the above-mentioned U.S. Pat. No. 8,492,696.

In the example shown in FIG. 1, the zero, first and second diffraction orders from grating 28 make up the projected pattern, while higher diffraction orders 32 are diffracted into the substrate volume of DOE 26. These higher diffraction orders may be reflected internally between the optical surfaces of DOE 26 until they reach and exit through a side surface 34 of the DOE. For example, in a polycarbonate substrate with index of refraction n=1.57, the minimum angle for total internal reflection is 39.5°, so that any orders diffracted from grating 28 at angles above 39.5° will be guided by internal reflection to the side faces of the DOE. Typically, side surface 34 is transparent and perpendicular to the optical surfaces of DOE 26. Alternatively, the high diffraction orders that are reflected inside the DOE may exit through a light-transmitting side surface oriented at any suitable angle that is not parallel to the optical surfaces.

An optical detector 38, such as a silicon photodiode, receives and senses a portion of the radiation that exits DOE 26 through side surface 34. In the pictured embodiment, a collection optic 36 focuses the radiation onto the detector. Alternatively, a front surface of the detector may be fixed in contact with the side surface of the DOE, as illustrated in FIGS. 2 and 3.

A controller 40 monitors the signal output by detector 38, which is indicative of the intensity of higher diffraction orders 32. This intensity, in turn, is an indicator of the efficiency of grating 28. Should the grating be degraded or fail entirely, the intensity of the higher diffraction orders will be affected, and the signal output by detector 38 will change accordingly. In most cases, the intensity of the higher orders will decrease as grating efficiency drops, but in some severe failure scenarios, the radiation scattered toward detector 38 will actually increase.

If the signal is outside a certain permitted range, and particularly if the signal changes by more than a certain threshold—either dropping below a predefined minimum level or exceeding a predefined maximum—controller 40 will inhibit the operation of radiation source 22, and may simply turn of the radiation source entirely. In this manner, controller 40 indirectly monitors the intensity of the zero diffraction order from grating 28, which becomes stronger as the grating efficiency degrades, and by virtue of this monitoring is able to prevent hazards that could otherwise occur due to DOE failure. To perform the above functions, controller 40 may comprise, for example, an embedded microcontroller or even a simple threshold-sensing logic device, which may be integrated with projector 20. Alternatively, the functions of controller 40 may be performed by a microprocessor, which also performs other functions in a system in which projector 20 is integrated.

Figure 2:
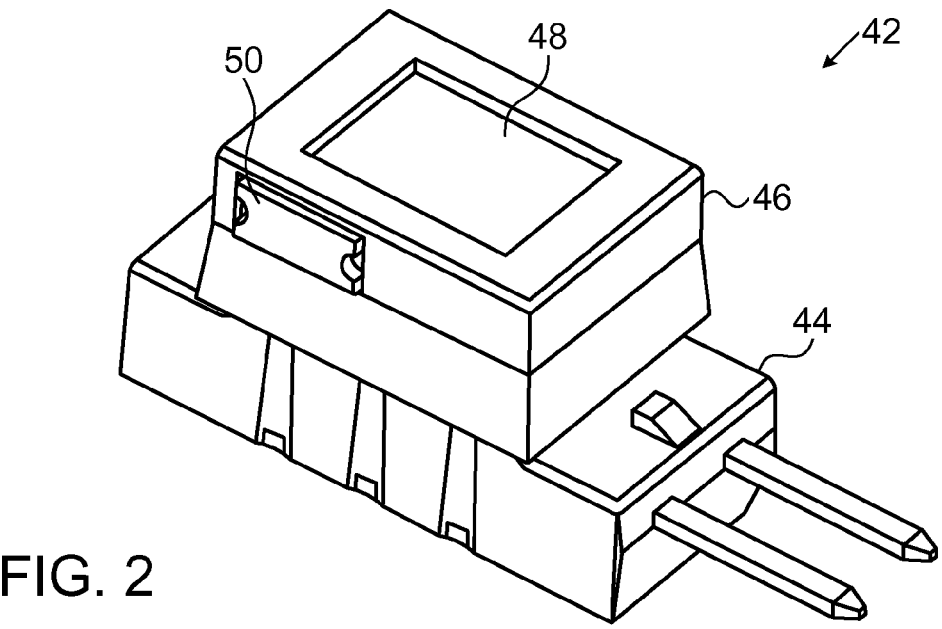
FIG. 2 is a schematic pictorial illustration of an optical projector with a beam monitor, in accordance with an embodiment of the present invention.
Figure 3:
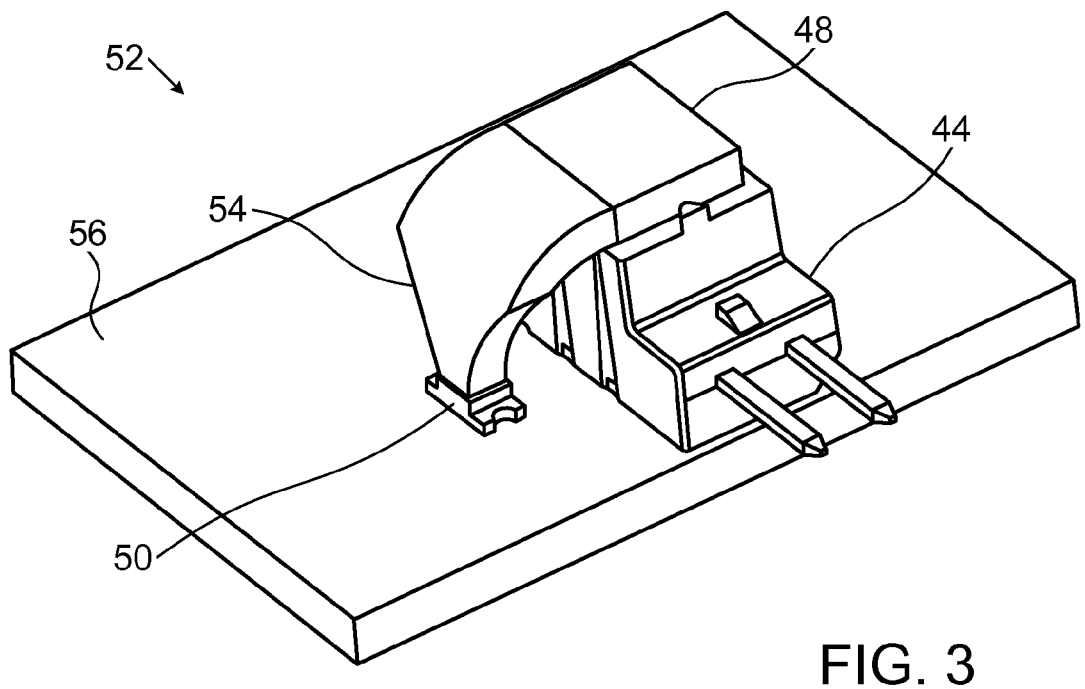
FIG. 3 is a schematic pictorial illustration of an optical projector with a beam monitor, in accordance with another embodiment of the present invention.

FIG. 2 is a schematic pictorial illustration of an optical projector 42 with a beam monitor, in accordance with an embodiment of the present invention. Projector comprises a housing 44, which contains and provides power and control signals to a radiation source, such as a VCSEL array (not shown in the figure). An optical assembly 46, mounted on housing 44, includes a DOE 48, which diffracts the radiation from the radiation source into a predefined pattern. A photodiode 50 is mounted on housing, facing inward, so as to receive high-order diffraction from the side surface of DOE 48.

FIG. 3 is a schematic pictorial illustration of an optical projector 52 with a beam monitor, in accordance with another embodiment of the present invention. In this case, housing 44 and photodiode 50 are both mounted on a substrate 56, such as a printed circuit board. Photodiode 50 has an extended front surface in the form of a light guide 54, which channels light from the side surface of DOE 48 to the photodiode.

Although the above embodiments relate to certain DOE configurations and certain applications of such DOEs, the use of an integral optical detector for monitoring a diffraction order emitted through the side surface of a DOE may likewise be used in other configurations and applications. Furthermore, although the disclosed embodiments relate specifically to applications involving projection of optical patterns, particularly for three-dimensional (3D) mapping, the principles of these embodiments may similarly be applied in other applications in which there is a need to monitor the diffraction performance of a DOE.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Optical apparatus, comprising:
 a diffractive optical element (DOE), comprising:
  multiple optical surfaces, which comprise at least an entrance surface and an exit surface;
  a side surface, which is not parallel to the optical surfaces of the DOE; and
  a grating, which is formed on at least one of the optical surfaces so as to receive radiation entering the DOE via the entrance surface and to diffract the radiation into a predefined pattern comprising multiple diffraction orders that exit the DOE via the exit surface; and
 an optical detector, which is positioned in proximity to the side surface so as to receive and sense an intensity of a high order of the radiation diffracted from the grating that passes through the side surface of the DOE.

2. The apparatus according to claim 1, wherein the side surface is perpendicular to the optical surfaces of the DOE.

3. The apparatus according to claim 1, wherein the optical detector comprises a front surface that is in contact with the side surface of the DOE.

4. The apparatus according to claim 1, wherein the optical surfaces of the DOE are configured so that the high order of the diffracted radiation reaches the side surface after reflecting internally within the DOE.

5. The apparatus according to claim 1, and comprising a controller, which is coupled to receive a signal from the optical detector that is indicative of the intensity of the high order of the diffracted radiation and to monitor a performance of the DOE responsively to the signal.

6. The apparatus according to claim 5, and comprising a radiation source, which is configured to direct the radiation toward the entrance surface of the DOE, wherein the controller is coupled to control an operation of the radiation source responsively to the monitored performance.

7. The apparatus according to claim 6, wherein the controller is configured to inhibit the operation of the radiation source when the signal is outside a predefined range.

8. The apparatus according to claim 7, wherein the diffraction orders that exit the DOE via the exit surface include a zero order, and wherein a change of the signal is indicative of an increase of an intensity of the zero order, and the controller is configured to inhibit the operation of the radiation source when the change exceeds a predefined threshold.

9. An optical method, comprising:
 transmitting radiation through a diffractive optical element (DOE), which comprises multiple optical surfaces, including at least an entrance surface and an exit surface, and which comprises a grating, which is formed on at least one of the optical surfaces so as to receive the radiation entering the DOE via the entrance surface and to diffract the radiation into a predefined pattern comprising multiple diffraction orders that exit the DOE via the exit surface; and
 receiving and sensing an intensity of a high order of the radiation diffracted from the grating that passes through a side surface of the DOE, which is not parallel to the optical surfaces of the DOE.

10. The method according to claim 9, wherein the side surface is perpendicular to the optical surfaces of the DOE.

11. The method according to claim 9, wherein the intensity is received by an optical detector in proximity to the side surface.

12. The method according to claim 11, wherein a front surface of the optical detector is in contact with the side surface of the DOE.

13. The method according to claim 9, wherein the optical surfaces of the DOE are configured so that the high order of the diffracted radiation reaches the side surface after reflecting internally within the DOE.

14. The method according to claim 9, wherein sensing the intensity of the high order of the diffracted radiation comprises monitoring a performance of the DOE responsively to the sensed intensity.

15. The method according to claim 14, wherein transmitting the radiation comprises directing the radiation from a radiation source toward the entrance surface of the DOE, and wherein the method comprises controlling an operation of the radiation source responsively to the monitored performance.

16. The method according to claim 15, wherein controlling the operation comprises inhibiting the operation of the radiation source when the signal is outside a predefined range.

17. The method according to claim 16, wherein the diffraction orders diffraction orders that exit the DOE via the exit surface include a zero order, and wherein a change of the signal is indicative of an increase of an intensity of the zero order, and wherein inhibiting the operation comprises turning off the radiation source when the change exceeds a predefined threshold.

\* \* \* \* \*